(12) United States Patent
Senger et al.

(10) Patent No.: US 11,260,095 B2
(45) Date of Patent: Mar. 1, 2022

(54) MODIFICATION OF PLANT LIPIDS CONTAINING PUFAS

(71) Applicant: BASF PLANT SCIENCE COMPANY GMBH, Ludwigshafen (DE)

(72) Inventors: Toralf Senger, Durham, NC (US); Carl Andre, Raleigh, NC (US)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 681 days.

(21) Appl. No.: 15/526,162

(22) PCT Filed: Nov. 13, 2015

(86) PCT No.: PCT/EP2015/076630
§ 371 (c)(1),
(2) Date: May 11, 2017

(87) PCT Pub. No.: WO2016/075325
PCT Pub. Date: May 19, 2016

(65) Prior Publication Data
US 2018/0291390 A1 Oct. 11, 2018

Related U.S. Application Data

(60) Provisional application No. 62/234,373, filed on Sep. 29, 2015, provisional application No. 62/079,622, filed on Nov. 14, 2014.

(51) Int. Cl.
| | | |
|---|---|---|
| *A61K 36/00* | (2006.01) | |
| *A61K 36/31* | (2006.01) | |
| *C12Q 1/6895* | (2018.01) | |
| *C12N 15/82* | (2006.01) | |
| *C12N 9/02* | (2006.01) | |
| *C12N 9/00* | (2006.01) | |
| *A61K 31/202* | (2006.01) | |

(52) U.S. Cl.
CPC ............ *A61K 36/31* (2013.01); *C12Q 1/6895* (2013.01); *A61K 31/202* (2013.01); *C12N 9/0071* (2013.01); *C12N 9/93* (2013.01); *C12N 15/8247* (2013.01); *C12Y 114/19* (2013.01); *C12Y 114/19003* (2013.01); *C12Y 114/19006* (2013.01); *C12Y 602/01003* (2013.01)

(58) Field of Classification Search
CPC .................................................. A61K 36/31
USPC .................................................. 424/755, 776
See application file for complete search history.

(56) References Cited

U.S. PATENT DOCUMENTS

| | | | |
|---|---|---|---|
| 5,627,289 A | 5/1997 | Jeromin et al. | |
| 6,303,849 B1 | 10/2001 | Potts et al. | |
| 6,689,880 B2 | 2/2004 | Chen et al. | |
| 6,733,974 B1 | 5/2004 | Feazel | |
| 6,740,488 B2 | 5/2004 | Rangwala et al. | |
| 6,818,807 B2 | 11/2004 | Trolinder et al. | |
| 6,825,400 B2 | 11/2004 | Behr et al. | |
| 6,893,826 B1 | 5/2005 | Hillyard et al. | |
| 6,900,014 B1 | 5/2005 | Weston et al. | |
| 7,423,198 B2 | 9/2008 | Yao et al. | |
| 8,999,411 B2 | 4/2015 | Froman et al. | |
| 2014/0220215 A1* | 8/2014 | Iassonova ................ A23D 9/00 426/541 |
| 2015/0299676 A1 | 10/2015 | Walsh et al. | |
| 2016/0369290 A1 | 12/2016 | Cirpus et al. | |

FOREIGN PATENT DOCUMENTS

| | | |
|---|---|---|
| AU | 2011289381 A1 | 1/2013 |
| CN | 101400798 A | 4/2009 |
| WO | WO-93/10241 A1 | 5/1993 |
| WO | WO-94/13814 A1 | 6/1994 |
| WO | WO-95/27791 A1 | 10/1995 |
| WO | WO-96/24674 A1 | 8/1996 |
| WO | WO-98/55631 A1 | 12/1998 |
| WO | WO-98/55632 A1 | 12/1998 |
| WO | WO-99/64616 A2 | 12/1999 |
| WO | WO-00/18889 A2 | 4/2000 |
| WO | WO-01/059128 A2 | 8/2001 |
| WO | WO-02/26946 A2 | 4/2002 |
| WO | WO-2002/052024 A2 | 7/2002 |
| WO | WO-2003/078639 A2 | 9/2003 |
| WO | WO-2003/089452 A2 | 10/2003 |
| WO | WO-2003/093482 A2 | 11/2003 |
| WO | WO-2004/071467 A2 | 8/2004 |
| WO | WO-2004/087902 A2 | 10/2004 |

(Continued)

OTHER PUBLICATIONS

Akermoun et al., Complex lipid biosynthesis: phospholipid synthesis, Biochemical Society Transactions 28: 713-5 (2000).
Bafor et al., Ricinoleic acid biosynthesis and triacylglycerol assembly in microsomal preparations from developing castor-bean (*Ricinus communis*) endosperm, Biochem. J., 280(Pt.2):507-14 (Dec. 1991).
Banas et al., Biosynthesis of an Acetylenic Fatty Acid in Microsomal Preparations from Developing Seeds of *Crepis alpina*. In: *Physiology, Biochemistry and Molecular Biology of Plant Lipids* (Williams et al. eds.) pp. 57-59. Kluwer Academic Press, Dordrecht (1997).
Bates et al., Acyl Editing and Headgroup Exchange Are the Major Mechanisms That Direct Polyunsaturated Fatty Acid Flux into Triacylglycerols. Plant Physiology 160: 1530-1539 (2012).
Bernert et al., Analysis of Partial Reactions in the Overall Chain Elongation of Saturated and Unsaturated Fatty Acids by Rat Liver Microsomes. J. Biol. Chem. 252, 6736-6744 (1977).

(Continued)

*Primary Examiner* — Qiuwen Mi
(74) *Attorney, Agent, or Firm* — Marshall, Gerstein & Borun LLP

(57) ABSTRACT

The present invention generally is concerned with the modification of plant lipids containing PUFAs. In this context, the invention is particularly concerned with plants and plant materials for such modifications, wherein the plants preferably are oilseed plants. Regarding plant parts, the invention is particularly concerned with seeds of such plants and preferably seeds of oilseed plants. The invention is also concerned with plant positions obtainable or obtained by the modification method of the invention, and with full stuff of feedstuff comprising such liquid compositions.

11 Claims, No Drawings

Specification includes a Sequence Listing.

(56) References Cited

FOREIGN PATENT DOCUMENTS

| | | | |
|---|---|---|---|
| WO | WO-2004/090123 A2 | 10/2004 | |
| WO | WO-2005/007845 A2 | 1/2005 | |
| WO | WO-2005/012316 A2 | 2/2005 | |
| WO | WO-2005/083053 A2 | 9/2005 | |
| WO | WO-2005/083093 A2 | 9/2005 | |
| WO | WO-2006/008099 A2 | 1/2006 | |
| WO | WO-2006/012325 A1 | 2/2006 | |
| WO | WO-2006/024509 A2 | 3/2006 | |
| WO | WO-2006/069710 A1 | 7/2006 | |
| WO | WO-2006/100241 A2 | 9/2006 | |
| WO | WO-2007/096387 A1 | 8/2007 | |
| WO | WO-2008/022963 A2 | 2/2008 | |
| WO | WO-2009/111263 A1 | 9/2009 | |
| WO | WO-2010/023202 A2 | 3/2010 | |
| WO | WO-2010023202 A2 * | 3/2010 | ............... C12N 9/00 |
| WO | WO-2010/066703 A2 | 6/2010 | |
| WO | WO-2011/006948 A1 | 1/2011 | |
| WO | WO-2011/161093 A1 | 12/2011 | |
| WO | WO-2013/049227 A2 | 4/2013 | |
| WO | WO-2013/153404 A2 | 10/2013 | |
| WO | WO-2013153404 A1 * | 10/2013 | ........... C12N 9/1029 |
| WO | WO-2013/185184 A2 | 12/2013 | |
| WO | WO-2015/089587 A1 | 6/2015 | |

OTHER PUBLICATIONS

Blombach et al., Acetohydroxyacid synthase, a novel target for improvement of L-lysine production by Corynebacterium glutamicum, Appl. Environ. Microbiol., 75(2):419-27 (Jan. 2009).

Broadwater et al., Desaturation and hydroxylation. Residues 148 and 324 of *Arabidopsis* FAD2, in addition to substrate chain length, exert a major influence in partitioning of catalytic specificity, J. Biol. Chem., 277(18):15613-20 (May 2002).

Broun et al., Catalytic plasticity of fatty acid modification enzymes underlying chemical diversity of plant lipids, Science, 282(5392):1315-7 (Nov. 1998).

Brown et al., Synthetic promoters for CHO cell engineering, Biotechnol. Bioeng., 111(8):1638-47 (Aug. 2014).

Calvo et al., Genetic connection between fatty acid metabolism and sporulation in Aspergillus nidulans, J. Biol. Chem., 276(28):25766-74 (Jul. 2001).

Certik et al., Desaturase-defective fungal mutants: useful tools for the regulation and overproduction of polyunsaturated fatty acids, Trends in Biotechnology, vol. 16, No. 12, Dec. 1, 1998, pp. 500-505.

Deal et al., Histone variants and modifications in plant gene regulation, Curr. Opin. Plant Biol., 14(2):116-22 (Apr. 2011).

Demeke et al., Influence of DNA extraction methods, PGR inhibitors and quantification methods on real-time PGR assay of biotechnology-derived traits, Anal. Bioanal. Chem., 396(6):1977-90 (Mar. 2010).

Denic et al., A molecular caliper mechanism for determining very long-chain fatty acid length, Cell, 130(4):663-77 (Aug. 2007).

Eiamsa-ard et al., Two novel Physcomitrella patens fatty acid elongases (ELOs): identification and functional characterization, Appl. Microbiol. Biotechnol., 97:3485-3497 (2013).

Fraser et al., Partial purification and photoaffinity labelling of sunflower acyl-CoA:lysophosphatidylcholine acyltransferase, Biochem. Soc. Trans., 28(6):715-8 (Dec. 2000).

Fukuda, Characterization of matrix attachment sites in the upstream region of a tobacco chitinase gene, Plant Mol. Biol., 39(5):1051-62 (Mar. 1999).

Giusto et al., Lipid metabolism in vertebrate retinal rod outer segments, Prog. Lipid Res., 39(4):315-91 (Jul. 2000).

Goffman, et al., "Genetic variation of tocopherol content in a germplasm collection of *Brassica napus* L.", Euphytica, vol. 125, May 2002, pp. 189-196.

Hamilton, A binary-BAC system for plant transformation with high-molecular-weight DNA, Gene, 200(1-2):107-16 (Oct. 1997).

Hattori et al., Experimentally determined sequence requirement of ACGT-containing abscisic acid response element, Plant Cell Physiol., 43(1):136-40 (Jan. 2002).

He et al, Agrobacterium-Mediated Transformation of Large DNA Fragments Using a BIBAC Vector System in Rice, Plant Molecular Biology Reporter, vol. 28, No. 4, Mar. 2, 2010, pp. 613-619.

Higo et al., Plant cis-acting regulatory DNA elements (PLACE) database: 1999, Nucleic Acids Res., 27(1):297-300 (Jan. 1999).

Hinnebusch, The scanning mechanism of eukaryotic translation initiation, Annu. Rev. Biochem., 83:779-812 (2014).

Horrocks et al., Health benefits of Docosahexaenoic acid (DHA), Pharmacol. Res., 40(3):211-25 (Sep. 1999).

Keller et al., Crystal structure of a bZIP/DNA complex at 2.2 A: determinants of DNA specific recognition, J. Mol. Biol., 254(4):657-67 (Dec. 1995).

Kim et al., Transcription factors that directly regulate the expression of CSLA9 encoding mannan synthase in *Arabidopsis thaliana*, Plant Mol. Biol., 84(4-5):577-87 (Mar. 2014).

Komori et al., Current status of binary vectors and superbinary vectors, Plant Physiol., 145(4):1155-60 (Dec. 2007).

Kong et al., Expression levels of domestic cDNA cassettes integrated in the nuclear genomes of various Chlamydomonas reinhardtii strains, J. Biosci. Bioeng., 117(5):613-6 (May 2014).

Kozak, Initiation of translation in prokaryotes and eukaryotes, Gene, 234(2):187-208 (Jul. 1999).

Lopez et al., Identification of novel motif patterns to decipher the promoter architecture of co-expressed genes in *Arabidopsis thaliana*, BMC Syst. Biol., 7 Suppl 3:S10 (Oct. 2013).

Lowenthal et al., Quantitative bottom-up proteomics depends on digestion conditions, Anal. Chem., 86(1):551-8 (Jan. 2014).

Machens et al., Identification of a novel type of WRKY transcription factor binding site in elicitor-responsive cis-sequences from *Arabidopsis thaliana*, Plant Mol. Biol., 84(4-5):371-85 (2014).

Makriyannis et al., Design and study of peptide-ligand affinity chromatography adsorbents: application to the case of trypsin purification from bovine pancreas, Biotechnol. Bioeng., 53(1):49-57 (Jan. 1997).

Mantle et al., Differentiation of Claviceps purpurea in axenic culture, J. Gen. Microbiol., 93(2):321-34 (Apr. 1976).

Meggendorfer et al., Functional nuclear topography of transcriptionally inducible extra-chromosomal transgene clusters, CHromosome Res., 18(4):401-17 (Jun. 2010).

Mey et al., The biotrophic, non-appressorium-forming grass pathogen Claviceps purpurea needs a Fus3/Pmk1 homologous mitogen-activated protein kinase for colonization of rye ovarian tissue, Mol. Plant Microbe Interact., 15(4):303-12 (Apr. 2002).

Meyer et al., Novel fatty acid elongases and their use for the reconstitution of docosahexaenoic acid biosynthesis, Journal of Lipid Research, 45:1899-1909 (2004).

Muino et al., Structural determinants of DNA recognition by plant MADS-domain transcription factors, Nucleic Acids Res., 42(4):2138-46 (Feb. 2014).

Murashige et al., A Revised Medium for Rapid Growth and Bio Assays with Tobacco Tissue Cultures. Physiologia Plantarum 15, 3:473-497 (1962).

Nakagawa et al., Diversity of preferred nucleotide sequences around the translation initiation codon in eukaryote genomes, Nucleic Acids Res., 36(3):861-71 (Feb. 2008).

Nishikata et al., Database construction for PromoterCAD: synthetic promoter design for mammals and plants, ACS Synth. Biol., 3(3):192-6 (Mar. 2014).

Parker et al., Local DNA topography correlates with functional noncoding regions of the human genome, Science, 324(5925):389-92 (Apr. 2009).

Petrie et al., Metabolic engineering Camelina sativa with fish oil-like levels of DHA, PLoS One, 9(1):e85061 (Jan. 2014).

Potts et al., Inheritance of fatty acid composition in *Brassica juncea*, Proceedings of the 10th International Rapeseed Congress, Sep. 26, 1999.

Proc et al., A quantitative study of the effects of chaotropic agents, surfactants, and solvents on the digestion efficiency of human plasma proteins by trypsin, J> Proteome Res., 9(10):5422-37 (Oct. 2010).

(56) References Cited

OTHER PUBLICATIONS

Ramamoorthy et al., Length and sequence dependent accumulation of simple sequence repeats in vertebrates: potential role in genome organization and regulation, Gene, 551(2):167-75 (Nov. 2014).
Schwender et al., "Rubisco without the Calvin cycle improves the carbon efficiency of developing green seeds", Nature, 432:779-82 (2004).
Shrestha et al., Int. J. Mol. Sci., Comparison of the substrate preferences of ω3 fatty acid desaturases for long chain polyunsaturated fatty acids, 20:3058 (2019).
Smith et al., Measurement of protein using bicinchoninic acid, Anal. Biochem., 150(1):76-85 (Oct. 1985).
Spector, Essentiality of fatty acids, Lipids, 34 Suppl: S1-3 (1999).
Stymne et al., Evidence for the reversibility of the acyl-CoA:lysophosphatidylcholine acyltransferase in microsomal preparations from developing safflower (Carthamus tinctorius L.) cotyledons and rat liver, Biochem. J., 233(2):305-14 (1984).
Sánchez-García et al., Differential temperature regulation of three sunflower microsomal oleate desaturase (FAD2) isoforms overexpressed in Saccharomyces cerevisia, Eur. J. Lipid Sci. Tech., 106:583-590 (2004).
Truksa et al., Molecular analysis of flax 2S storage protein conlinin and seed specific activity of its promoter, Plant Physiol, and Biochem., 41:141-7 (2003).
Tudzynski et al., Biotechnology and genetics of ergot alkaloids, Appl. Microbiol. Biotechnol., 57(5-6):593-605 (Dec. 2001).
Tumaney et al., Synthesis of azidophospholipids and labeling of lysophosphatidylcholine acyltransferase from developing soybean cotyledons, Biochim. Biophys. Acta, 1439(1):47-56 (Jul. 1999).
Wachter et al., Synthetic CpG islands reveal DNA sequence determinants of chromatin structure, Elife, 3:e03397 (Sep. 2014).
Wang et al., ω3 fatty acid desaturases from microorganisms: structure, function, evolution, and biotechnological use, App. Microbiol., 97:10255-62 (2013).
Wijesundra, The influence of triacylglycerol structure on the oxidative stability of polyunsaturated oils, Lipid Technology, 20:199-202 (2008).
Yamashita et al., ATP-independent fatty acyl-coenzyme A synthesis from phospholipid: coenzyme A-dependent transacylation activity toward lysophosphatidic acid catalyzed by acyl-coenzyme A:lysophosphatidic acid acyltransferase, J. Biol. Chem., 276(29):26745-52 (Jul. 2001).
Abidi et al., "Effect of Genetic Modification on the Distribution of Minor Constituents in Canola Oil", Journal of the American Oil Chemists' Society, vol. 76, Issue 4, pp. 463-467 (Apr. 1999).
Arondel, et al., "Map-based Cloning of a Gene Controlling Omega-3 Fatty Acid Desaturation in Arabidopsisc", Science vol. 258, Issue 5086, Nov. 20, 1992, pp. 1353-1355.
Bai, et al., "X-ray Structure of a Mammalian Stearoyl-CoA Desaturase", Nature, Aug. 2015, vol. 524, pp. 252-256.
Bligh, et al., "A Rapid Method of Total Lipid Extraction and Purification", Canadian Journal of Biochemistry and Physiology, vol. 37, Issue 1, 1959, pp. 911-917.
Cutler, et al., "Abscisic Acid: Emergence of a Core Signaling Network", Annual Review of Plant Biology, vol. 61, 2010, pp. 651-679.
Database EMBL [Online] 5, "Rattus Norvegicus clone CH230-506F12, Working Draft Sequence, Unordered Pieces.", XP002754369, retrieved from EBI accession No. EM_HTG:AC142370 (Mar. 29, 2003).
Database EMBL [Online], "Mus Musculus Domesticus DNA, BAG Clone: B6Ng01-175K07, 3' End.", XP002754370, retrieved from EBI accession No. EM_GSS:GA003396, created Feb. 6, 2011).
De Block, et al., "Transformation of Brassica Napus and Brassica Oleracea Using Agrobacterium Tumefaciens and the Expression of the Bar and Neo Genes in the Transgenic Plants", Plant Physiol., v.91(2):694-701 (1989).
Dolde, et al., "Tocopherols in Breeding Lines and Effects of Planting Location, Fatty Acid Composition, and Temperature During Development", JAOCS, 76:349-55 (Mar. 1999).
Domergue, et al., Acyl Carriers Used as Substrates by the Desaturases and Elongases Involved in Very Long-chain Polyunsaturated Fatty Acids Biosynthesis Reconstituted in Yeast, J. Biol. Chem., 278(37):35115-26 (2003).
Domergue, et al., "In Vivo Characterization of the First Acyl-CoA Δ6-Desaturase from a Member of the Plant Kingdom, the Microalga Ostreococcus Tauri", Biochem. J., 389(Pt. 2):483-90 (2005).
Dubos, et al., "Integrating Bioinformatic Resources to Predict Transcription Factors Interacting with Cis-Sequences Conserved in Co-Regulated Genes", BMC Genomics, 15:317 (2014).
Focks, et al., "Wrinkled1: A Novel, Low-Seed-Oil Mutant of Arabidopsis with a Deficiency in the Seed-Specific Regulation of Carbohydrate Metabolism", Plant Physiol., 118(1):91-101 (1998).
Griffiths, et al., Delta 6- and Delta 12-desaturase Activities and Phosphatidic Acid Formation in Microsomal Preparations from the Developing Cotyledons of Common Borage (Borango officinalis), Biochem. J., 252(3):641-7 (1988).
International Preliminary Report on Patentability, International Application No. PCT/EP2015/076596, dated May 16, 2017.
International Preliminary Report on Patentability, PCT Application No. PCT/EP2015/076608, completed Feb. 28, 2017.
International Preliminary Report on Patentability, PCT application No. PCT/EP2015/076605, dated May 16, 2017.
International Search Report and Written Opinion for PCT Patent Application No. PCT/EP2015/076596, dated Mar. 11, 2016, 15 pages.
International Search Report and Written Opinion for PCT Patent Application No. PCT/EP2015/076605, dated Feb. 24, 2016, 13 pages.
International Search Report and Written Opinion for PCT Patent Application No. PCT/EP2015/076608, dated Mar. 9, 2016, 13 pages.
Jain, et al., "Identification of a Novel Lysophospholipid Acyltransferase in Saccharomyces cerevisiae", J. Biol. Chem., 282(42):30562-9 (2007).
Kargiotidou, et al., "Low Temperature and Light Regulate Delta 12 Fatty Acid Desaturases (FAD2) at a Transcriptional Level in Cotton (Gossypium hirsutum)", J. Exp. Bot., 49(8):2043-56 (2008).
Knutzon, et al., "Identification of Delta5-dehydratase from Mortierella Alpina by Heterologous Expression in Bakers' Yeast and Canola", J. Biol. Chem., 273(45):29360-6 (1998).
Li, et al., "Correlations between Tocopherol and Fatty Acid Components in Germplasm Collections of Brassica Oilseeds", Journal of Agricultural and Food Chemistry, 61:34-40 (2013).
Meesapyodsuk, et al., "The Front-end Desaturase: Structure, Function, Evolution and Biotechnological Use", Lipids, vol. 47, Issue 3, Mar. 2012, pp. 227-237.
O'Malley, et al., "An Adapter Ligation-Mediated Pcr Method for High-Throughput Mapping of T-DNA Inserts in the Arabidopsis Genome", Nature Protocols, vol. 2, Issue 11, 2007, pp. 2910-2917.
Okayasu, et al., "Purification and Partial Characterization of Linoleoyl-CoA Desaturase from Rat Liver Microsomes", Archives of Biochemistry and Biophysics, 206(1):21-8 (1981).
Okuley, et al., "Arabidopsis FAD2 Gene Encodes the Enzyme that is Essential for Polyunsaturated Lipid Synthesis", The Plant Cell Online, vol. 6, Issue 1, Jan. 1994, pp. 147-158.
Paul, et al., "Members of the Arabidopsis FAE1-like 3-Ketoacyl-CoA Synthase Gene Family Substitute for the Elop Proteins of Saccharomyces cerevisiae", J. Biol. Chem., 281(14):9018-29 (2006).
Qi, et al., "Production of Very Long Chain Polyunsaturated Omega-3 and Omega-6 Fatty Acids in Plants", Nature Biotechnology, vol. 22, Issue 6, Jun. 2004, pp. 739-745.
Quek, et al., "Commercial Extraction of Vitamin E from Food Sources" The Encyclopedia of Vitamin E, Eds. Preedy, et al., CABI Publishers, Oxford, U.K., 2007, pp. 140-152.
Riekhof, et al., "Lysophosphatidylcholine Metabolism in Saccharomyces cerevisiae The Role of P-Type Atpases in Transport and in Broad Specificity Acyltransferase in Acylation", J. Biol. Chem., 282(51):36853-61 (2007).
Ruiz-Lopez, et al., "Successful High-level Accumulation of Fish Oil Omega-3 Long-Chain Polyunsaturated Fatty Acids in a Transgenic Oilseed Crop",Plant J., 77(2):198-208 (2014).

(56) References Cited

OTHER PUBLICATIONS

Ruuska, et al., "Contrapuntal Networks of Gene Expression during *Arabidopsis* Seed Filling", The Plant Cell Online, vol. 14, Issue 6, Jun. 2002, pp. 1191-1206.
Rychlik, et al, "A computer program for choosing optimal oligonudeotides for filter hybridization, sequencing and in vitro amplification of DNA", Nucleic Acids Research, 17(21):8543-51 (1989).
Sarkar, et al., "Specificity Determinants for the Abscisic Acid Response Element", FEBS Open Bio, vol. 3, Issue 1, Jan. 1, 2013, pp. 101-105.
Shanklin, et al., "Desaturation and Related Modifications of Fatty Acids1", Annual Review of Plant Physiology and Plant Molecular Biology, vol. 49, Jun. 1998, pp. 611-641.
Shanklin, et al., "Stearoyl-acyl-carrier-protein desaturase from Higher Plants is Structurally Unrelated to the Animal and Fungal Homologs", Proc. Natl. Acad. Sci. USA, 88(6):2510-4 (1991).
Strittmatter et al., "Purification and Properties of Rat Liver Microsomal Stearyl Coenzyme A Desaturase", Proc. Natl. Acad. Sci. USA, 71(11):4565-9 (1974).
Stymne, et al., "Biosynthesis of y-linolenic Acid in Cotyledons and Microsomal Preparations of the Developing Seeds of Common Borage (Borago Officinalis)", Biochem. J., 240(2):385-93 (1986).
Tamaki, et al., "LPT1 Encodes a Membrane-bound O-Acyltransferase Involved in the Acylation of Lysophospholipids in the Yeast *Saccharomyces Cerevisiae*", J. Biol. Chem., 282(47):34288-98 (2007).
Tang, et al., "Oleate Desaturase Enzymes of Soybean: Evidence of Regulation Through Differential Stability and Phosphorylation", Plant J., 44(3):433-46 (2005).
Wang, et al., "Crystal Structure of Human Stearoyl-Coenzyme a Desaturase in Complex with Substrate", Nature Structural & Molecular Biology, vol. 22, 2015, pp. 581-585.
Wu, et al., "Stepwise Engineering to Produce High Yields of Very Long-Chain Polyunsaturated Fatty Acids in Plants", Nature Biotechnology, vol. 23, Issue 8, 2005, pp. 1013-1017.
Xiao, et al., "Characterization of the Promoter and 5'-UTR Intron of Oleic Acid Desaturase (FAD2) Gene in *Brassica Napus*", Gene, vol. 545, Issue 1, Jul. 2014, pp. 45-55.
Browse et al., Fatty acid composition of leaf lipids determined after combined digestion and fatty acid methyl ester formation from fresh tissue, Anal. Biochem., 152(1):141-5 (1986).
Cahoon et al., Biosynthetic origin of conjugated double bonds: production of fatty acid components of high-value drying oils in transgenic soybean embryos, Proc. Natl. Acad. Sci. USA, 96(22):12935-40 (1999).
Datar et al. Cell and Cell Debris Removal: Centrifugation and Crossflow Filtration, pp. 472-503 IN: Rehm et al. (eds.), Biotechnology, Second, Completely Revised Edition, vol. 3 (Bioprocessing) edited by Stephanopoulos, Weinheim, Germany: VCH (1993).
Fujiwara et al., Seed-specific repression of GUS activity in tobacco plants by antisense RNA, Plant Mol. Biol., 20(6):1059-69 (1992).
Hull et al., Analysis of the promoter of an abscisic acid responsive late embryogenesis abundant gene of *Arabidopsis thaliana*, Plant Sci., 14:181-92 (1996).
International Preliminary Report on Patentability, International Application No. PCT/EP2015/076630, dated May 16, 2017.
International Search Report and Written Opinion, International Application No. PCT/EP2015/076630, dated Mar. 7, 2016.
Livak et al., Analysis of relative gene expression data using real-time quantitative PCR and the 2(-Delta Delta C(T)) Method, Methods, 25(4):402-8 (2001).
Vilardell et al., Regulation of the rab17 gene promoter in transgenic *Arabidopsis* wild-type, ABA-deficient and ABA-insensitive mutants, Plant Mol. Biol., 24(4):561-9 (1994).

\* cited by examiner

SEQUENCE LISTING

```
<160> NUMBER OF SEQ ID NOS: 39

<210> SEQ ID NO 1
<211> LENGTH: 30
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(30)
<223> OTHER INFORMATION: /mol_type="DNA" /note="Oligo: Table PCR1;
      D12Des(PS-GA) / D12DESPS-138Fam" /organism="Artificial Sequence"
<220> FEATURE:
<221> NAME/KEY: source
<222> LOCATION: (1)..(30)

<400> SEQUENCE: 1
tgcctggata cctcttcttc aacgctactg                                    30

<210> SEQ ID NO 2
<211> LENGTH: 25
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(25)
<223> OTHER INFORMATION: /mol_type="DNA" /note="Oligo: Table PCR1;
      d6-Des(Otfebit) / D6DES-653FAM" /organism="Artificial Sequence"
```

```
<400> SEQUENCE: 2
actccatgca caacaagcac cacgc                                        25

<210> SEQ ID NO 3
<211> LENGTH: 25
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(25)
<223> OTHER INFORMATION: /mol_type="DNA" /note="Oligo: Table PCR1;
      d6Elo (Pp GA) / D6Elo-296-FAM" /organism="Artificial Sequence"

<400> SEQUENCE: 3
tgtgcgtggg tatcgcttac caagc                                        25

<210> SEQ ID NO 4
<211> LENGTH: 27
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(27)
<223> OTHER INFORMATION: /mol_type="DNA" /note="Oligo: Table PCR1;
      d6Elo(Tp GA) / D6Elo-280-FAM" /organism="Artificial Sequence"

<400> SEQUENCE: 4
aggaacggat acaccgttat gccatgc                                      27

<210> SEQ ID NO 5
<211> LENGTH: 22
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(22)
<223> OTHER INFORMATION: /mol_type="DNA" /note="Oligo: Table PCR1;
      d5DES(Tc_GA) / D5DES-652-FAM" /organism="Artificial Sequence"

<400> SEQUENCE: 5
ttggagcacg atgtggattt ga                                           22

<210> SEQ ID NO 6
<211> LENGTH: 27
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(27)
<223> OTHER INFORMATION: /mol_type="DNA" /note="Oligo: Table PCR1;
      d5DES(Tc_GA)3 / D5DES-1147-Fam" /organism="Artificial Sequence"

<400> SEQUENCE: 6
caaccgctcc acaattcagg ttcaagg                                      27

<210> SEQ ID NO 7
<211> LENGTH: 27
<212> TYPE: DNA
<213> ORGANISM: Artificial Sequence
<220> FEATURE:
<223> OTHER INFORMATION: Synthetic polynucelotide
```

```
<220> FEATURE:
<221> NAME/KEY: source
<222> LOCATION: (1)..(27)
<223> OTHER INFORMATION: /mol_type="DNA" /note="Oligo: Table PCR1;
      o3DES(Pi_GA2) / o3DES-594FAM" /organism="Artificial Sequence"

<400> SEQUENCE: 7
cgctcacttc ttcgttgctg gactctc                                              27

<210> SEQ ID NO 8
<211> LENGTH: 19
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(19)
<223> OTHER INFORMATION: /mol_type="DNA" /note="Oligo: Table PCR1;
      o3DES(PIR_GA) / o3DESPIR-198FAM" /organism="Artificial Sequence"

<400> SEQUENCE: 8
atcatctctc tcggagttc                                                       19

<210> SEQ ID NO 9
<211> LENGTH: 24
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(24)
<223> OTHER INFORMATION: /mol_type="DNA" /note="Oligo: Table PCR1;
      d5Elo(Ot_GA3) / E011" /organism="Artificial Sequence"

<400> SEQUENCE: 9
tgacaaacaa gccaccaagc ccaa                                                 24

<210> SEQ ID NO 10
<211> LENGTH: 29
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(29)
<223> OTHER INFORMATION: /mol_type="DNA" /note="Oligo: Table PCR1;
      d4DES(TC_GA) / D4DES-Tc-FAM" /organism="Artificial Sequence"

<400> SEQUENCE: 10
tgcttcccca atgtacgttg ctaggttct                                            29

<210> SEQ ID NO 11
<211> LENGTH: 14
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(14)
<223> OTHER INFORMATION: /mol_type="DNA" /note="Oligo: Table PCR1;
      d4Des(Eg_GA) / D4DES-Eg-FAM" /organism="Artificial Sequence"

<400> SEQUENCE: 11
aaggcacatc ctcc                                                            14
```

```
<210> SEQ ID NO 12
<211> LENGTH: 27
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(27)
<223> OTHER INFORMATION: /mol_type="DNA" /note="Oligo: Table PCR1;
      d4Des(Pl_GA2) / D4DES-PI-770FAM" /organism="Artificial Sequence"

<400> SEQUENCE: 12
agcttctttt cttggacgcc cttgagc                                              27

<210> SEQ ID NO 13
<211> LENGTH: 25
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(25)
<223> OTHER INFORMATION: /mol_type="DNA" /note="Oligo: Table PCR1;
      GPI / Exp3-78-YAK" /organism="Artificial Sequence"

<400> SEQUENCE: 13
ggattcgaca ttccatcggc tttga                                                25

<210> SEQ ID NO 14
<211> LENGTH: 23
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(23)
<223> OTHER INFORMATION: /mol_type="DNA" /note="Oligo: Table PCR2;
      D12Des(PS-GA) / D12DESPS-112F" /organism="Artificial Sequence"

<400> SEQUENCE: 14
cgtgtacatg ttggttgttg gat                                                  23

<210> SEQ ID NO 15
<211> LENGTH: 22
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(22)
<223> OTHER INFORMATION: /mol_type="DNA" /note="Oligo: Table PCR2;
      d6-Des(Otfebit) / D6DES-629F" /organism="Artificial Sequence"

<400> SEQUENCE: 15
tggctggatc tggagatatg tg                                                   22

<210> SEQ ID NO 16
<211> LENGTH: 24
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(24)
<223> OTHER INFORMATION: /mol_type="DNA" /note="Oligo: Table PCR2;
      d6Elo (Pp GA) / D6Elo-271F" /organism="Artificial Sequence"
```

```
<400> SEQUENCE: 16
ttctgcttcg ctttgtctct ttac                                              24

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(20)
<223> OTHER INFORMATION: /mol_type="DNA" /note="Oligo: Table PCR2;
      d6Elo(Tp_GA) / D6Elo-259F" /organism="Artificial Sequence"

<400> SEQUENCE: 17
gaggctggat tcctcgctta                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(20)
<223> OTHER INFORMATION: /mol_type="DNA" /note="Oligo: Table PCR2;
      d5DES(Tc_GA) / D5DES-631Fa" /organism="Artificial Sequence"

<400> SEQUENCE: 18
caccacgctg ctccaaacag                                                   20

<210> SEQ ID NO 19
<211> LENGTH: 22
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(22)
<223> OTHER INFORMATION: /mol_type="DNA" /note="Oligo: Table PCR2;
      d5DES(Tc_GA)3 / D5DES-1120F" /organism="Artificial Sequence"

<400> SEQUENCE: 19
acttccaaat cgagcaccac tt                                                22

<210> SEQ ID NO 20
<211> LENGTH: 21
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(21)
<223> OTHER INFORMATION: /mol_type="DNA" /note="Oligo: Table PCR2;
      o3DES(Pi_GA2) / o3DES-572F" /organism="Artificial Sequence"

<400> SEQUENCE: 20
ccgctgtggt tatctctttg c                                                 21

<210> SEQ ID NO 21
<211> LENGTH: 26
<212> TYPE: DNA
<213> ORGANISM: Artificial Sequence
<220> FEATURE:
```

```
<223> OTHER INFORMATION: Synthetic polynucelotide
<220> FEATURE:
<221> NAME/KEY: source
<222> LOCATION: (1)..(26)
<223> OTHER INFORMATION: /mol_type="DNA" /note="Oligo: Table PCR2;
      o3DES(PIR_GA) / o3DESPIR-160F" /organism="Artificial Sequence"

<400> SEQUENCE: 21
cttgggaggc tatgtatgtt agaaga                                        26

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(20)
<223> OTHER INFORMATION: /mol_type="DNA" /note="Oligo: Table PCR2;
      d5Elo(Ot_GA3) / MA54" /organism="Artificial Sequence"

<400> SEQUENCE: 22
gcaatcgttg gtagccatga                                               20

<210> SEQ ID NO 23
<211> LENGTH: 22
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(22)
<223> OTHER INFORMATION: /mol_type="DNA" /note="Oligo: Table PCR2;
      d4DES(TC_GA) / D4DES-Tc-F" /organism="Artificial Sequence"

<400> SEQUENCE: 23
caaatcgatg ctgagtgcag at                                            22

<210> SEQ ID NO 24
<211> LENGTH: 23
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(23)
<223> OTHER INFORMATION: /mol_type="DNA" /note="Oligo: Table PCR2;
      d4Des(Eg_GA) / D4DES-EG-F" /organism="Artificial Sequence"

<400> SEQUENCE: 24
tgacaagtaa gccatccgtc agt                                           23

<210> SEQ ID NO 25
<211> LENGTH: 23
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(23)
<223> OTHER INFORMATION: /mol_type="DNA" /note="Oligo: Table PCR2;
      d4Des(Pl_GA2) / D4DES-PI-746-F" /organism="Artificial Sequence"

<400> SEQUENCE: 25
ctggtgaggc tatgtacgct ttt                                           23
```

<210> SEQ ID NO 26
<211> LENGTH: 25
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(25)
<223> OTHER INFORMATION: /mol_type="DNA" /note="Oligo: Table PCR2;
      GPI / Exp 3-52F" /organism="Artificial Sequence"

<400> SEQUENCE: 26
gatgaatatc ctcctgatgc taacc                                          25

<210> SEQ ID NO 27
<211> LENGTH: 26
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(26)
<223> OTHER INFORMATION: /mol_type="DNA" /note="Oligo: Table PCR3;
      D12Des(PS-GA) / D12DESPS-201R" /organism="Artificial Sequence"

<400> SEQUENCE: 27
tgagacctag actttcccca gtactt                                         26

<210> SEQ ID NO 28
<211> LENGTH: 22
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(22)
<223> OTHER INFORMATION: /mol_type="DNA" /note="Oligo: Table PCR3;
      d6-Des(Otfebit) / D6DES-706R" /organism="Artificial Sequence"

<400> SEQUENCE: 28
ccatatcgtg cctcactttt tg                                             22

<210> SEQ ID NO 29
<211> LENGTH: 24
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(24)
<223> OTHER INFORMATION: /mol_type="DNA" /note="Oligo: Table PCR3;
      d6Elo (Pp GA) / D6Elo-345R" /organism="Artificial Sequence"

<400> SEQUENCE: 29
ccacaaggaa tatctccagg tgat                                           24

<210> SEQ ID NO 30
<211> LENGTH: 21
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(21)
<223> OTHER INFORMATION: /mol_type="DNA" /note="Oligo: Table PCR3;

```
        d6Elo(Tp GA) / D6Elo-330R" /organism="Artificial Sequence"

<400> SEQUENCE: 30
tggatcgttc acgttgaagt g                                              21

<210> SEQ ID NO 31
<211> LENGTH: 20
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(20)
<223> OTHER INFORMATION: /mol_type="DNA" /note="Oligo: Table PCR3;
        d5DES(Tc_GA) / D5DES-695R" /organism="Artificial Sequence"

<400> SEQUENCE: 31
aaagcaacga gtggcaaggt                                                20

<210> SEQ ID NO 32
<211> LENGTH: 24
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(24)
<223> OTHER INFORMATION: /mol_type="DNA" /note="Oligo: Table PCR3;
        d5DES(Tc_GA)3 / D5DES-1200R" /organism="Artificial Sequence"

<400> SEQUENCE: 32
agagagcctc aactcttgga gaga                                           24

<210> SEQ ID NO 33
<211> LENGTH: 24
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(24)
<223> OTHER INFORMATION: /mol_type="DNA" /note="Oligo: Table PCR3;
        o3DES(Pi_GA2) / o3DES-652R" /organism="Artificial Sequence"

<400> SEQUENCE: 33
tcttaagtcc caactggaga gaca                                           24

<210> SEQ ID NO 34
<211> LENGTH: 24
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(24)
<223> OTHER INFORMATION: /mol_type="DNA" /note="Oligo: Table PCR3;
        o3DES(PIR_GA) / o3DESPIR-262R" /organism="Artificial Sequence"

<400> SEQUENCE: 34
aaaccaagga gcgtcaagtc taga                                           24

<210> SEQ ID NO 35
<211> LENGTH: 20
<212> TYPE: DNA
<213> ORGANISM: Artificial Sequence
```

```
<220> FEATURE:
<223> OTHER INFORMATION: Synthetic polynucelotide
<220> FEATURE:
<221> NAME/KEY: source
<222> LOCATION: (1)..(20)
<223> OTHER INFORMATION: /mol_type="DNA" /note="Oligo: Table PCR3;
      d5Elo(Ot_GA3) / MA55" /organism="Artificial Sequence"

<400> SEQUENCE: 35
cgtgtaccac cacgctttgt                                                     20

<210> SEQ ID NO 36
<211> LENGTH: 24
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(24)
<223> OTHER INFORMATION: /mol_type="DNA" /note="Oligo: Table PCR3;
      d4DES(TC_GA) / D4DES-Tc-988R" /organism="Artificial Sequence"

<400> SEQUENCE: 36
aacacggtca aagccttcat aatc                                                24

<210> SEQ ID NO 37
<211> LENGTH: 22
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(22)
<223> OTHER INFORMATION: /mol_type="DNA" /note="Oligo: Table PCR3;
      d4Des(Eg_GA) / D4DES-Eg-R" /organism="Artificial Sequence"

<400> SEQUENCE: 37
actttTcacc accgacgaag tt                                                  22

<210> SEQ ID NO 38
<211> LENGTH: 18
<212> TYPE: DNA
<213> ORGANISM: Artificial Sequence
<220> FEATURE:
<223> OTHER INFORMATION: Synthetic polynucelotide
<220> FEATURE:
<221> NAME/KEY: source
<222> LOCATION: (1)..(18)
<223> OTHER INFORMATION: /mol_type="DNA" /note="Oligo: Table PCR3;
      d4Des(Pl_GA2) / D4DES-PI-817R" /organism="Artificial Sequence"

<400> SEQUENCE: 38
cctcccacct ccaagcaa                                                       18

<210> SEQ ID NO 39
<211> LENGTH: 22
<212> TYPE: DNA
<213> ORGANISM: Artificial Sequence
<220> FEATURE:
<223> OTHER INFORMATION: Synthetic polynucelotide
```

```
<220> FEATURE:
<221> NAME/KEY: source
<222> LOCATION: (1)..(22)
<223> OTHER INFORMATION: /mol_type="DNA" /note="Oligo: Table PCR3;
      GPI / Exp 3-128R" /organism="Artificial Sequence"

<400> SEQUENCE: 39
cttgcatgat gatcaggaaa gc                                              22
```

MODIFICATION OF PLANT LIPIDS CONTAINING PUFAS

This application is a National Stage application of International Application No. PCT/EP2015/076630, filed Nov. 13, 2015, which claims the benefit of U.S. Provisional Patent Application No. 62/079,622, filed Nov. 14, 2014 and U.S. Provisional Patent Application No. 62/234,373, filed Sep. 29, 2015, which are incorporated herein by reference in their entirety.

INCORPORATION BY REFERENCE OF MATERIAL SUBMITTED ELECTRONICALLY

This application incorporates by reference in its entirety a computer-readable nucleotide/amino acid sequence listing identified as one 14,416 byte ASCII (text) file named "H150220_Seqlisting.txt", created May 9, 2017.

FIELD OF THE INVENTION

The present invention generally is concerned with the modification of plant lipids containing PUFAs. In this context, the invention is particularly concerned with plants and plant materials for such modifications, wherein the plants preferably are oilseed plants. Regarding plant parts, the invention is particularly concerned with seeds of such plants and preferably seeds of oilseed plants. The invention is also concerned with plant compositions obtainable or obtained by the modification method of the invention, and with foodstuff of feedstuff comprising such liquid compositions.

BACKGROUND OF THE INVENTION

It is generally recognised that polyunsaturated fatty acids ("PUFAs") convey health benefits. In this context, EPA and DHA are particularly coveted; they are used as dietary supplements for example to alleviate cardiovascular or neurological pathological conditions or ailments. Polyunsaturated fatty acids are currently predominantly obtained from fish oils, because wild-type plants lack the required enzymes to produce polyunsaturated fatty acids, particularly EPA and DHA, in sufficient quantities. Efforts have been made to produce polyunsaturated fatty acids in plants and particularly in oilseed plants.

The production of EPA and DHA is a metabolic pathway wherein fatty acids are treated by desaturases and elongases to produce ever longer and more unsaturated fatty acids. A depiction of the pathway can be found in WO 2006/012325, FIG. 9, and WO 2005/083093, FIG. 1. The desaturases and elongases involved in the pathway generally react both on omega-3 and omega-6 polyunsaturated fatty acids. One intermediate in the production of EPA and DHA generally is arachidonic acid. This polyunsaturated fatty acid is generally undesirable in dietary compositions, foodstuff and feedstuff due to its involvement in inflammatory processes. Thus, it is generally desired to obtain compositions with a high content of EPA and/or DHA and a low content of arachidonic acid. However, as arachidonic acid is a metabolit in the production of DHA and because arachidonic acid can be converted by omega-3 desaturases to and from EPA, it is generally not possible to avoid concomitant production of arachidonic acid in transgenic plant metabolism.

It is thus an object of the present invention to provide materials and methods for reducing the content of arachidonic acid in lipid compositions containing EPA and/or DHA. In particular, it is an object of the invention to provide materials and methods for reducing the content of arachidonic acid in plant lipid compositions, preferably in lipid compositions obtainable or obtained from oilseed plants.

BRIEF SUMMARY OF THE INVENTION

The invention therefore provides extracted plant lipid compositions comprising eicosapentaenoic acid (EPA) and docosahexaenoic acid (DHA) and optionally arachidonic acid (ARA), wherein
a) the content of EPA is at least 5% higher than of ARA, and/or
b) the sum of contents of EPA+DHA is at least 7% higher than ARA and/or
c) the content of ARA is less than 4% and the content of EPA is more than 7% and the content of DHA is more than 2%.

The invention also provides plants or parts thereof, comprising lipids including eicosapentaenoic acid (EPA) and docosahexaenoic acid (DHA) and optionally arachidonic acid (ARA), wherein
a) the content of EPA is at least 5% higher than of ARA, and/or
b) the sum of contents of EPA+DHA is at least 7% higher than ARA and/or
c) the content of ARA is less than 4% and the content of EPA is more than 7% and the content of DHA is more than 2%.

Also, the invention provides plants or parts thereof, comprising lipids including eicosapentaenoic acid (EPA) and docosahexaenoic acid (DHA) and arachidonic acid (ARA), wherein, when the plant or part thereof is grown, the content of ARA decreases while preferably the content of EPA and/or DHA increases.

According to the invention is also provided a plant comprising a nucleic acid comprising
a) a Delta-5 elongase gene under the control of a promoter such that expression of the Delta-5 elongase gene is maintained or increased in late stage seed development, and/or
b) a Delta-5 desaturase gene under the control of a promoter such that expression of the Delta-5 desaturase gene is reduced or prevented in late stage seed development.

The invention also provides seeds of a plant of the present invention.

Further, the invention provides plant lipid compositions obtainable or obtained by a process comprising the steps of
a) growing a plant of the present invention at least until the lipids content of ARA has decreased and preferably the lipids content of EPA and/or DHA has increased, and
b) harvesting the plant or a part thereof and
c) extracting lipids composition from the harvested material to obtain said lipid composition.

The invention also provides foodstuff or feedstuff comprising a lipid composition of the present invention.

Furthermore, the invention provides methods of altering plant lipids composition, comprising the step of growing a plant of the invention to produce lipids including eicosapentaenoic acid (EPA) and docosahexaenoic acid (DHA) and arachidonic acid (ARA), wherein the step of growing and lipids production is continued until the content of ARA has decreased while preferably the content of EPA and/or DHA has increased.

And the invention provides methods of producing a plant lipid composition, comprising the steps of
a) growing plants of the invention, b) harvesting the plants or a part thereof when the lipids content of ARA has decreased and preferably the lipids content of EPA and/or DHA has increased.

DETAILED DESCRIPTION OF THE INVENTION

The invention provides extracted plant lipid compositions. The lipid compositions comprise EPA and DHA. The extracted plant lipid compositions will generally also comprise ARA, even though this compound is generally not desired as a component but is normally unavoidable due to its function as intermediate metabolite in the production of EPA and/or DHA.

According to the invention, the content of EPA is at least 5% higher than the content of ARA. Unless indicated otherwise, in the context of the present invention a comparison of content numbers is to mean the difference between the respective percentage numbers; such difference is sometimes also called a difference in points percentage. Thus, when the content of EPA in an exemplary composition is for example 7 wt.-%, the content of ARA in the composition is at most 2 wt.-% of total fatty acids of the lipids composition.

It is a particular advantage of the present invention to provide means for the production of lipid compositions exhibiting such strong difference in contents between EPA and ARA. It was particularly surprising that such a marked difference could be maintained in plant lipid compositions, that is in lipid compositions produced in plant material or extracted therefrom as described herein, because both ARA and EPA are produced by the same class of enzymes, that is Delta-5 desaturases, and typically a Delta-5 desaturase producing EPA will also produce ARA. Also, ARA and EPA are converted into each other by action of omega 3 desaturases naturally present in material or introduced into the plant genome for the purposes of polyunsaturated fatty acid production. It was therefore expected that the composition of plant lipids could not be tilted in favour of high EPA contents without also increasing ARA content. However, the inventors have surprisingly found and provide herein a way not only to increase the EPA content without correspondingly also increasing the content of unwanted ARA; instead, the invention surprisingly provides means for actually decreasing the lipid content of ARA during lipid production already in the plant. Such decrease in ARA content at a time of continuing synthesis of EPA had not been observed or been expected to be possible at all before.

The invention therefore also advantageously provides extracted plant lipid compositions wherein the sum of contents of EPA plus DHA is at least 7% higher than the content of ARA. Providing such a marked difference in contents is even more surprising as EPA is converted into DHA by the action of Delta-5 elongase and Delta 4 desaturase. Thus, EPA is effectively consumed in the production of DHA; it is therefore a particular advantage of the present invention to maintain a high difference in the contents of EPA, DHA and ARA. As described hereinafter, achieving such high difference in contents is possible by the unexpected depletion of ARA in plant lipids during ongoing synthesis of EPA and DHA.

The invention also provides extracted plant lipid compositions wherein the content of ARA is less than 4% and the content of EPA is more than 7%. Even more preferably, the invention provides extracted plant lipid compositions wherein the content of ARA is less than 4%, the content of EPA is more than 7% and the content of DHA is more than 2%. Such compositions are particularly advantageous results of the unexpected mechanism of plant lipid production provided by the invention and simultaneously attain a high EPA/DHA content and a low ARA content.

Polyunsaturated fatty acids (PUFAs) are generally known to the skilled person, important polyunsaturated fatty acids are categorised into an omega-3, omega-6 and omega-9 series, without any limitation intended. Polyunsaturated fatty acids of the omega-6 series include, for example, and without limitation, linoleic acid (18:2 n-6; LA), gamma-linolenic acid (18:3 n-6; GLA), di-homo-gamma-linolenic acid (C20:3 n-6; DGLA), arachidonic acid (C20:4 n-6; ARA), adrenic acid (also called docosatetraenoic acid or DTA; C22:4 n-6) and docosapentaenoic acid (C22:5 n-6). Polyunsaturated fatty acids of the omega-3 series include, for example and without limitation, alpha-linolenic acid (18:3 n-3, ALA), stearidonic acid (18:4 n-3; STA or SDA), eicosatrienoic acid (C20:3 n-3; ETA), eicosatetraenoic acid (C20:4 n-3; ETA), eicosapentaenoic acid (C20:5 n-3; EPA), docosapentaenoic acid (C22:5 n-3; DPA) and docosahexaenoic acid (C22:6 n-3; DHA). Polyunsaturated fatty acids also include fatty acids with greater than 22 carbons and 4 or more double bonds, for example and without limitation, C28:8 (n-3). Polynsaturated fatty acids of the omega-9 series include, for example, and without limitation, mead acid (20:3 n-9; 5,8,11-eicosatrienoic acid), erucic acid (22:1 n-9; 13-docosenoic acid) and nervonic acid (24:1 n-9; 15-tetracosenoic acid). Further polyunsaturated fatty acids are eicosadienoic acid (C20:2d11,14; EDA) and eicosatrienoic acid (20:3d11,14,17; ETrA).

Within the context of the present invention, lipids content is expressed as weight percentage of a specific fatty acid relative to total fatty acids determined in the respective lipids composition. Preferably, the total fatty acids tested for are: 14:0, 16:0, 16:1n-7, 16:1n-9, 16:3n-3, 17:0, 18:0, 18:1n-7, 18:1n-9, 18:2n-6 (LA), 18:2n-9, 18:3n-3 (ALA), 18:3n-6 (GLA), 18:4n-3 (SDA), 20:0, 20:1n-9, 20:2n-6, 20:2n-9, 20:3n-3, 20:3n-6 (DGLA), 20:3n-9, 20:4n-3 (ETA), 20:4n-6 (ARA), 20:5n-3 (EPA), 22:0, 22:1n-9, 22:2n-6, 22:4n-3, 22:4n-6, 22:5n-3 (DPA), 22:5n-6, 22:6n-3 (DHA), 24:0 and 24:1n-9.

It is a particular advantage of the present invention that the lipids contents described herein, unless explicitly noted otherwise, are determined without artificial enrichment or depletion of one or more fatty acids; the lipid content of a fatty acid is thus substantially the same as in the plant or part thereof prior to extraction.

The extracted lipid preferably is in the form of an oil, wherein at least 90%, more preferably least 95% and even more preferably at least about 98%, or between 95% and 98%, by weight of the oil is the lipid. Such oils can be obtained from plant material by methods known to the skilled person and/or as described herein.

According to the invention, the extracted plant lipid composition is a composition produced by a plant or plant material—preferred ways of producing such lipid compositions in plants and plant materials are also described herein-, and extracted from such lipids and optionally purified. Preferably, the extracted plant lipid composition is a composition to which no additional fatty acids have been added. It is a particular advantage of the present invention that the high difference between the contents of EPA and ARA can be achieved without adding "foreign" EPA to the composition, that is without addition of EPA that has not been produced by the plant or plant material the extract is obtained from. In particular, the contents of EPA and DHA can be achieved according to the invention without addition of fish oil or of corresponding polyunsaturated fatty acids obtained from fish oil.

Within the context of the present invention, reference is made to plants and to corresponding plant material. The plants (and correspondingly the plant material) refer to preferably is of family Brassicaceae. It is a particular advantage of the present invention that the lipid compositions of the present invention can be produced in and extracted from plants of this family, because such plants allow for the production of high amounts of fatty acids particularly in their seed oil. Also, many species belonging to this family have a long tradition as crop plants, the contents of their oil is thus generally considered useful for consumption and/or easy to obtain and purify for technical purposes or for purposes of consumption.

Plants according to the invention and corresponding plant material preferably belong to the tribus Aethionemeae, Alysseae, Alyssopsideae, Anastaticeae, Anchonieae, Aphragmeae, Arabideae, Asteae, Biscutelleae, Bivonaeeae, Boechereae, Brassiceae, Buniadeae, Calepineae, Camelineae, Cardamineae, Chorisporeae, Cochlearieae, Coluteocarpeae, Conringieae, Cremolobeae, Crucihimalayeae, Descurainieae, Dontostemoneae, Erysimeae, Euclidieae, Eudemeae, Eutremeae, Halimolobeae, Heliophileae, Hesperideae, Iberideae, Isatideae, Kernereae, Lepidieae, Malcolmieae, Megacarpaeeae, Microlepidieae, Noccaeeae, Notothlaspideae, Oreophytoneae, Physarieae, Schizopetaleae, Scoliaxoneae, Sisymbrieae, Smelowskieae, Stevenieae, Thelypodieae, Thlaspideae, Turritideae or Yinshanieae, and even more preferably belong genus *Ammosperma, Brassica, Brassica×Raphanus, Cakile, Carrichtera, Ceratocnemum, Coincya, Cordylocarpus, Crambe, Crambella, Didesmus, Diplotaxis, Douepea, Enarthrocarpus, Eremophyton, Eruca, Erucaria, Erucastrum, Euzomodendron, Fezia, Foleyola, Fortuynia, Guiraoa, Hemicrambe, Henophyton, Hirschfeldia, Kremeriella, Moricandia, Morisia, Muricaria, Nasturtiopsis, Orychophragmus, Otocarpus, Physorhynchus, Pseuderucaria, Psychine, Raffenaldia, Raphanus, Rapistrum, Rytidocarpus, Savignya, Schouwia, Sinapidendron, Sinapis, Succowia, Trachystoma, Vella* or *Zilla*. Plants of the aforementioned taxa belong to the family of Brassicaceae and thus can allow for the easy manifestation of the advantages described above in view of said taxonomic family.

Even more preferably the plant or plant material according to the invention belongs to a crop plant of genus *Camelina* or *Brassica*. Plants of these genera have traditionally been used in agriculture, their oils have been used for human or animal consumption for a long time. Also, agricultural practices in view of these genera have long been established, for example materials and methods for defense against fungi, insects and weeds. Thus, the production of plant lipids according to the invention in such genera is made particularly easy for the person skilled in agriculture.

Even more preferably a plant and correspondingly plant material according to the invention belongs to any of the species *Camelina sativa, Brassica aucheri, Brassica balearica, Brassica barrelieri, Brassica carinata, Brassica carinata×Brassica napus, Brassica carinata×Brassica rapa, Brassica cretica, Brassica deflexa, Brassica desnottesii, Brassica drepanensis, Brassica elongata, Brassica fruticulosa, Brassica gravinae, Brassica hilarionis, Brassica* hybrid *cultivar, Brassica incana, Brassica insularis, Brassica juncea, Brassica macrocarpa, Brassica maurorum, Brassica montana, Brassica napus* (rape, canola), *Brassica napus×Brassica rapa, Brassica nigra, Brassica oleracea, Brassica oleracea×Brassica rapa* subsp. *pekinensis, Brassica oxyrrhina, Brassica procumbens, Brassica rapa, Brassica rapa×Brassica nigra, Brassica repanda, Brassica rupestris, Brassica ruvo, Brassica souliei, Brassica spinescens, Brassica tournefortii* or *Brassica villosa*, even more preferably to any of the species *Brassica carinata, Brassica carinata×Brassica napus* or *Brassica napus*, most preferably of species *Brassica napus*. Plants of genus *Brassica napus* are also known as rape seed or canola and have a long tradition as a cheap and readily available source of plant oils and lipids fit for human or animal consumption.

Particularly preferred plants and plant materials are derived from transgenic *Brassica* event LBFLFK deposited as ATCC Designation "PTA-121703" as described herein, *Brassica* event LBFLFK contains two insertions of the binary T-plasmid VC-LTM593-1qcz rc as described in the examples section, or from transgenic *Brassica* event LBFDAU deposited as ATCC Designation "PTA-122340" as also described herein. For these events, particularly high contents of EPA and DHA can be achieved together with low contents of ARA.

Plants and plant materials also preferred according to the invention can be obtained by propagation of these events into other germplasms of plants of genus *Camelina* and even more preferably of genus *Brassica*. It is particularly preferred to use as plants and plant materials according to the invention plants resulting from a crossing of a transgenic event according to the invention, particularly of the event LBLFK, with plants of the species to *Brassica carinata*, even more preferably after backcrossing into *Brassica napus*. For such plants particularly high contents of EPA and/or DHA and low contents of ARA in the plant lipids according to the invention can be achieved.

According to the invention, the content of ARA preferably decreases by at least 0.5% during growth of the plant or plant material, preferably during seed development. Thus, by analysing the composition of plant lipids in said plant or plant material, a peak of ARA content can be observed. For example, when a peak content of ARA of 4% is observed, the plant or plant material is harvested only after the content of ARA has decreased to at most 3.5%. It is an advantage of the present invention that a reduction in lipids content of ARA by 0.5 percentage points can be achieved without compromising total lipids production and particularly without compromising the amount and content of EPA and/or DHA obtainable from such plant or plant material.

Preferably, when the plant or plant material of the invention is grown, the lipids content of EPA is maintained even during the reduction of ARA content. Even more preferably the lipids content of EPA increases by at least 1% during the period in which the content of ARA is reduced. Thus, for example the lipids content of EPA in plant seeds increases from 6% to 7% while simultaneously the lipids content of ARA in said plant material decreases from 4% to at most 3.5%. Even more preferably, the lipids content of EPA and DHA increase during the period of reduction of ARA lipids content when the plant or plant material of the present invention is grown. As noted herein before, it is a particular advantage that the present invention allows for such ongoing synthesis of EPA and DHA even though the content of the metabolic intermediate ARA is reduced.

As described above, the plants and plant material of the present invention preferably are oilseed plants. When the plants of the present invention are grown, it is preferred that they reach their maximum ARA lipids content before late stage seed development. Thus, sufficient time remains for the plant of the present invention to produce in its seed the desired quantities and contents of EPA and/or DHA while reducing the lipids content of ARA. According to the invention, the maximum of ARA lipids content is preferably reached in the developing seeds within 25 to 35 days after flowering where the plants of the present invention belong to species *Brassica napus*. Correspondingly late stage seed development preferably starts 38 days after flowering in *Brassica napus*, even more preferably 36 days and even more preferably 35 days after flowering. The skilled person understands that oilseed plants develop many flowers and that individual flowers start to bloom at different days. Thus, the term "days after flowering" refers to the days after flowering of the individual flower and not to the first flower detected on for example a field of plants of the present invention.

A plant or plant material according to the present invention preferably comprises a nucleic acid comprising
a) a Delta-5 elongase gene under the control of a promoter such that expression of the Delta-5 elongase gene is maintained or increased in late stage seed development, and/or
b) a Delta-5 desaturase gene under the control of a promoter such that expression of the Delta-5 desaturase gene is reduced or prevented in late stage seed development.

The inventors have found that by carefully regulating the expression particularly of Delta-5 elongase activity it is possible to achieve the desired reduction in ARA lipids content while maintaining ongoing synthesis of EPA and/or DHA.

The promoters according to the present invention preferably are seed specific promoters. Gene expression can be regulated by any means available to the skilled person. For example, gene expression can be achieved by creating the appropriate construct topology such that transformed nucleic acids (also called "T-DNA" in the art) will, by their very own arrangement of promoters, genes and terminators (collectively also called "expression cassette") achieve the desired regulation pattern. For example, an expression cassette comprising a promoter and operably linked thereto a Delta-5 elongase gene located in the vicinity of another promoter exhibiting strong late stage seed development gene expression can allow for maintained or increased expression of the Delta-5 elongase gene in late stage seed development. This is particularly so where the expression cassette comprising the Delta-5 elongase gene is separated from one border of integrated T-DNA by at most one expression cassette and from the other border of the T-DNA by at least 5 expression cassettes. This way the T-DNA is long enough to effectively insulate the expression cassettes of the T-DNA from, teen effects of the plant chromosome the T-DNA has integrated into. Preferably, the expression cassette comprising the Delta-5 the gene is separated from one border of the T-DNA by at most 3, more preferably 1 or 2 and even more preferably by 1 other expression cassette. For the purposes of the present invention, the expression cassette is preferred to in this paragraph contain genes required for the synthesis of polyunsaturated fatty acids and particularly genes coding for desaturases and elongases.

Increased Delta-5 elongase gene expression can also be achieved by the action of an inductor, such that at least one Delta-5 elongase gene is under the control of an inducible promoter; increase can also be achieved by removal of a repressor, such that the repressor is only being produced during early stages of seed development. Preferably, at least one Delta-5 elongase gene is additionally present and expressed under the control of a constitutively and strongly active promotor to achieve a high Delta-5 elongase gene expression also in early and mid seed development stages.

Decreased Delta-5 desaturase expression can be correspondingly achieved by T-DNA topology and/or by placing a Delta-5 desaturase gene under the control of an inducible promoter, wherein the inductor is not or to a lesser extent produced during late seed development, and/or by placing a Delta-5 desaturase gene under the control of a repressible promoter wherein the repressor is produced predominantly or only during late stage seed development.

Examples of corresponding promoters, inductors and repressors and their interaction are described in Hull et al., Plant Science 114, 181-192, Fujiwara et al., Plant Molecular Biology 20, 1059-1069 and Vilardell et al., Plant Molecular Biology 24, 561-569, all incorporated herein by reference.

The invention also provides seeds of a plant of the present invention. Such seeds are useful for planting of new plants of the present invention to produce polyunsaturated fatty acids. Seeds of the present invention are also useful for extraction purposes to obtain and extracted plant lipid composition of the present invention. In each case, the benefits described above can be achieved by the seeds of the present invention.

The invention also provides a plant lipid composition obtainable or obtained by a process comprising the steps of
a) growing a plant of the present invention at least until the lipids content of ARA has decreased and preferably the lipids content of EPA and/or DHA has increased, and
b) harvesting the plant or a part thereof and
c) extracting lipids composition from the harvested material to obtain said lipid composition.

In such process, the beneficial reduction of ARA content in plant lipids provided for by the present invention can be achieved and the corresponding benefits for plant lipid compositions can be materialised.

The process optionally also comprises the step of storing of harvested material, preferably of plant seeds. It is a particular advantage of the present invention that the plant seeds can be stored without compromising the amount and composition of plant seed oils and lipids. This was particularly surprising because polyunsaturated fatty acids are particularly prone to oxidation. Thus, it is advantageous that the plant seeds according to the present invention obtained as harvested material in said process can be stored for example for a month or at least for 7 days at ambient temperatures without loss of seed oil content and particularly without decrease of EPA and/or DHA in seed lipids and seed oil.

The process preferably also comprises the steps of threshing and collecting of seats. Particularly for plants of genus *Brassica* that a seeds are produced in house gutter and thus need to be separated from unwanted plant material. It is an advantage it is an advantage of the present invention that the seeds can be separated from unwanted plant material for example by threshing without compromising polyunsaturated fatty acid amount and composition in seed lipids and seed oil.

In the process, extraction preferably is performed using pressure and most preferably under an atmosphere with reduced oxygen content compared to ambient temperature; preferably, extraction is performed in the absence of oxygen, for example under a protective atmosphere. Corresponding extraction procedures are known to the skilled person, some extraction procedures are also described herein.

In the process harvesting of plant materials and preferably harvesting of seeds is preferably effected on ripe seeds, that is in late stage seed development. In ripe seeds the lipids content of ARA has had enough time to decrease and the contents of EPA and/or DHA could be increased. When such process is applied on plants of the invention of genus *Brassica*, harvesting is done preferably after 30 days after first flowering, preferably after 35 days, even more preferably after 40 days, even more preferably after 42 days, even more preferably on or after 43 days and even more preferably after or on 44 days and even more preferably on or after 45 and even more preferably on or after 46 days after first flowering of the plants.

The process preferably further comprises degumming, deodorising, bleaching, decolourising, drying, winterizing and/or fractionating of the extracted lipids to obtain said lipid composition. This way unwanted impurities of the lipids and/or oil can be removed. Corresponding processes and techniques are known to the skilled person.

The invention also provides foodstuff or feedstuff comprising a lipid composition of the invention. Such food—and feedstuff benefit from the high EPA and/or DHA lipids content and low ARA lipids content achieved by the present invention.

Correspondingly, the invention also provides a method of altering plant lipids composition, comprising the step of growing a plant pf the present invention to produce lipids including eicosapentaenoic acid (EPA) and docosahexaenoic acid (DHA) and arachidonic acid (ARA), wherein the step of growing and lipids production is continued until the content of ARA has decreased while preferably the content of EPA and/or DHA has increased. As described above, the content of ARA is preferably decreased by at least 0.5% and preferably is finally at most 4%, preferably is at most 3% and even more preferably at most 2.6% by weight of total lipids. Also as described above, the content of EPA is preferably increased by at least 1% and preferably is finally at least 7%, even more preferably at least 7.5% of total lipids.

The invention also provides a method of producing a plant lipid composition, comprising the steps of
a) growing plants of the present invention,
b) harvesting the plants or a part thereof when the lipids content of ARA has decreased and preferably the lipids content of EPA and/or DHA has increased.

The method allows to materialize the advantages and benefits described herein.

Preferably, *Brassica* plants of the present invention are grown on a field of commercial scale, preferably at least one acre of size. After 25 days after first appearance of flowers, samples of developing seeds and their lipids are analysed as described herein. Over the next 15 days, preferably over the next 10 days, at least two additional samples of developing seeds are taken and their lipids are also analysed. This way the peak of ARA lipids content can be detected and harvesting can be appropriately delayed to allow the plants of the invention to decrease ARA content and increase EPA and/or DHA content in the lipids of developing seeds.

Also, the invention provides a method of producing seed, comprising the steps of
a) growing plants of the present invention, and
b) harvesting seeds of the plants when the lipids content of ARA has decreased and preferably the lipids content of EPA and/or DHA has increased.

The method allows to materialize the advantages and benefits described herein.

The invention is hereinafter further described by way of examples; the examples are provided for illustrative purposes only and are not intended to limit the invention or the scope of the claims.

EXAMPLES

Example 1: Plant Growth and Sampling

Homozygous T3 plants of event LBFLFK (containing a two copies VC-LTM593-1qcz rc), homozygous T3 plants of event LBFGKN (containing one copy of VC-LTM593-1qcz rc), homozygous T4 plants of event LANPMZ (containing one copy each of VC-LJB2197-1qcz and VC-LLM337-1qcz rc) and homozygous T4 plants of event LAODDN (containing one copy each of VC-LJB2755-2qcz rc and VC-LLM391-2qcz rc) were sown in the field. Plants of the events were obtained and propagated as described in the examples of the priority documents; these are included herein by reference. All events comprise one gene coding for a Delta-5 elongase based on that obtained from *Ostreococcus tauri* ("d5Elo OT_GA3"). All events further contain one gene coding for a Delta-5 desaturase based on that obtained from *Thraustochytrium* sp. ("d5Des Tc_GA2"). Events LBFLFK and LBFGKN contain a further copy of the Delta-5 desaturase gene under the control of another promoter (SETL instead of Conlinin). In the week following the date of first flower, individual racemes were visibly marked on the stem just above the most recently opened flower. For every raceme, the three pods immediately below the mark were considered to be the same age (i.e. flowered or were pollinated on the same day). Starting at 14 days after marking and until 46 days after marking, the three pods below the mark on each raceme were collected at various time points. At each time point, approximately 150 pods from 50 individual plants were sampled. Each individual plant was sampled only once in its lifespan. Immature seeds were dissected from the pods immediately after removal from the raceme and were promptly frozen on dry ice. The age of the seeds was determined by the age of the mark on the raceme, meaning that the three pods (and the seeds inside) taken from immediately below a 15 day-old mark were assumed to be 15 days after flowering. For each event, at each time point, seeds from about 150 pods were pooled into a single sample. For analysis, each seed sample was pulverized to powder while still frozen, and the powder was dispensed into aliquot amounts to be used as technical replicates for lipid analysis and gene expression analysis by quantitative real time PCR.

Example 2: Lipid Extraction and Lipid Analysis of Plant Oils

Lipids were extracted as described in the standard literature including Ullman, Encyclopedia of Industrial Chemistry, Bd. A2, S. 89-90 und S. 443-613, VCH: Weinheim (1985); Fallon, A., et al., (1987) "Applications of HPLC in Biochemistry" in: Laboratory Techniques in Biochemistry and Molecular Biology, Bd. 17; Rehm et al. (1993) Biotechnology, Bd. 3, Kapitel III: "Product recovery and purification", S. 469-714, VCH: Weinheim; Belter, P. A., et al. (1988) Bioseparations: downstream processing for Biotechnology, John Wiley and Sons; Kennedy, J. F., und Cabral, J. M. S. (1992) Recovery processes for biological Materials, John Wiley and Sons; Shaeiwitz, J. A., und Henry, J. D. (1988) Biochemical Separations, in: Ullmann's Encyclopedia of Industrial Chemistry, Bd. B3; Kapitel 11, S. 1-27, VCH: Weinheim; and Dechow, F. J. (1989) Separation and purification techniques in biotechnology, Noyes Publications.

It is acknowledged that extraction of lipids and fatty acids can be carried out using other protocols than those cited above, such as described in Cahoon et al. (1999) Proc. Natl. Acad. Sci. USA 96 (22):12935-12940, and Browse et al. (1986) Analytic Biochemistry 152:141-145. The protocols used for quantitative and qualitative analysis of lipids or fatty acids are described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) u.d.T.: Progress in the Chemistry of Fats and Other Lipids CODEN.

The fatty acids analysed were: 14:0, 16:0, 16:1n-7, 16:1n-9, 16:3n-3, 17:0, 18:0, 18:1n-7, 18:1n-9, 18:2n-6 (LA), 18:2n-9, 18:3n-3 (ALA), 18:3n-6 (GLA), 18:4n-3 (SDA), 20:0, 20:1n-9, 20:2n-6, 20:2n-9, 20:3n-3, 20:3n-6 (DGLA), 20:3n-9, 20:4n-3 (ETA), 20:4n-6 (ARA), 20:5n-3 (EPA), 22:0, 22:1n-9, 22:2n-6, 22:4n-3, 22:4n-6, 22:5n-3 (DPA), 22:5n-6, 22:6n-3 (DHA), 24:0, 24:1n-9.

The content (levels) of fatty acids is expressed throughout the present invention as percentage (weight of a particular fatty acid) of the (total weight of all fatty acids).

Example 3: Quantitative Real Time PCR Protocol

RNA was extracted according to the protocol "SG-MA_0007-2009 RNA isolation" using Spectrum Plant Total RNA-KIT part number STRN50 (SIGMA-ALDRICH GmbH, Munich, Germany). In average the concentration of total RNA was about 450 ng/μl. The 260/280 ratio was at 2.2 and the 260/230 ratio at 2.3.

For cDNA synthesis for qPCR 1 μg of total RNA was treated with DNAseI (DEOXYRIBUNUCLEASE I (AMP-D1, Amplification Grade from SIGMA-Aldrich, GmbH) according to the supplier's protocol. After DNAseI treatment, the reverse transcription reaction was performed with the SuperScript™ III First-Strand Synthesis SuperMix for qRT-PCR (Invitrogen, Cat. No. 11752-250) and with a combination of oligo dT and random hexamers to ensure thorough and even representation of all transcripts, regardless of length.

Transcript measurement by quantitative real time PCR was carried out using procedures considered standard to those skilled in the art; see Livak and Schmittgen (2001).

The qPCR reactions were done as simplex TaqMan reactions. The endogenous reference gene was isolated in house and used due to predicted stability of the transcript based on the observed stability of the transcript corresponding to the orthologue in Arabidopsis thaliana during development. The Brassica napus ortholog was isolated and the gene, SEQ ID, was part of the glycosyl-phosphatidylinositol aminotransferase pathway (GPI). The cDNA reactions, described above, were diluted 1:4. 2 μl cDNA, which corresponded to 25 ng of total RNA, was used per 10 μl qPCR reaction with JumpStart TAQ ReadyMix (P2893-400RXN Sigma-Aldrich, GmbH). Primer/probe concentrations were 900 nmol for forward and reverse primer and 100 nmol TaqMan probe. The TaqMan probes for targets of interest were labeled with FAM/BHQ1, and the reference gene was labeled with Yakima Yellow/BHQ1.

Each qPCR assay included a 1:1 dilution curve (5 dilution steps) with cDNA from the pool VC-RTP10690-1qcz_F, a no template control, three-RT controls (VC-RTP10690-1qcz_F, VC-LTM593-1qcz rc (~4w) and co-transformation VC-LJB2197-1qcz+VC-LLM337-1qcz rc). From each pool three independent aliquots of cDNA were measured as technical repeats. The ABI PRISM® 7900 sequence detection system (Applied Biosystem) was used with the following PCR Conditions:

| Initial denaturation | 95° C. for 300 seconds | 1 cycle |
| Amplification | 95° C. for 15 seconds/60° C. for 60 seconds | repete for 40 cycles |

The raw data were the Ct values for the target and the endogenous reference gene, respectively. The dCt values were calculated by subtraction: Ct(GOI)−Ct(Ref). The Reference dCt value was set to equal zero, which was interpreted as meaning that if there was no difference between GPI and the gene of interest (dCt=0) the expression was =1. The fold expression was equal to $2^{-dCt}$ (where the dCt=(Ct (GOI)−Ct(Ref)−0)). Three samples from each pool were taken and the geometric mean was calculated. The slopes of dilution curves were calculated for each gene of interest and the endogenous reference gene (GPI) as a measure for the amplification efficiency. Table PCR1, Table PCR2 and Table PCR3 indicate the probes and primers used to amplify the genes for qPCR assays.

TABLE PCR1

Probes used in the qPCR reactions

| Target of Interest | Probe Name | Probe Oligo |
|---|---|---|
| D12Des(PS-GA) | D12DESPS-138Fam | TGCCTGGATACCTCTTCTTCAACGCTACTG |
| d6-Des(Otfebit) | D6DES-653FAM | ACTCCATGCACAACAAGCACCACGC |
| d6Elo(Pp GA) | D6Elo-296-FAM | TGTGCGTGGGTATCGCTTACCAAGC |
| d6Elo(Tp GA) | D6Elo-280-FAM | AGGAACGGATACACCGTTATGCCATGC |
| d5DES(Tc_GA) | D5DES-652-FAM | TTGGAGCACGATGTGGATTTGA |
| d5DES(Tc_GA)3' | D5DES-1147-Fam | CAACCGCTCCACAATTCAGGTTCAAGG |
| o3DES(Pi_GA2) | o3DES-594FAM | CGCTCACTTCTTCGTTGCTGGACTCTC |
| o3DES(PIR_GA) | o3DESPIR-198FAM | ATCATCTCTCTCGGAGTTC |
| d5Elo(Ot_GA3) | E011 | TGACAAACAAGCCACCAAGCCCAA |
| d4DES(TC_GA) | D4DES-Tc-FAM | TGCTTCCCCAATGTACGTTGCTAGGTTCT |

TABLE PCR1-continued

Probes used in the qPCR reactions

| Target of Interest | Probe Name | Probe Oligo |
| --- | --- | --- |
| d4Des(Eg_GA) | D4DES-Eg-FAM | AAGGCACATCCTCC |
| d4Des(PI_GA2) | D4DES-PI-770FAM | AGCTTCTTTTCTTGGACGCCCTTGAGC |
| GPI | Exp3-78-YAK | GGATTCGACATTCCATCGGCTTTGA |

TABLE PCR2

Forward primers used in qPCR

| Target of Interest | Forward Primer Name | Forward Primer Oligo |
| --- | --- | --- |
| D12Des(PS-GA) | D12DESPS-112F | CGTGTACATGTTGGTTGTTGGAT |
| d6-Des(Otfebit) | D6DES-629F | TGGCTGGATCTGGAGATATGTG |
| d6Elo(Pp_GA) | D6Elo-271F | TTCTGCTTCGCTTTGTCTCTTTAC |
| d6Elo(Tp_GA) | D6Elo-259F | GAGGCTGGATTCCTCGCTTA |
| d5DES(Tc_GA) | D5DES-631Fa | CACCACGCTGCTCCAAACAG |
| d5DES(Tc_GA)3' | D5DES-1120F | ACTTCCAAATCGAGCACCACTT |
| o3DES(Pi_GA2) | o3DES-572F | CCGCTGTGGTTATCTCTTTGC |
| o3DES(PIR_GA) | o3DESPIR-160F | CTTGGGAGGCTATGTATGTTAGAAGA |
| d5Elo(Ot_GA3) | MA54 | GCAATCGTTGGTAGCCATGA |
| d4DES(TC_GA) | D4DES-Tc-F | CAAATCGATGCTGAGTGCAGAT |
| d4Des(Eg_GA) | D4DES-EG-F | TGACAAGTAAGCCATCCGTCAGT |
| d4Des(PI_GA2) | D4DES-PI-746-F | CTGGTGAGGCTATGTACGCTTTT |
| GPI | Exp 3-52F | GATGAATATCCTCCTGATGCTAACC |

TABLE PCR3

Reverse primers used for qPCR

| Target of Interest | Reverse Primer Name | Reverse Primer Oligo |
| --- | --- | --- |
| D12Des(PS-GA) | D12DES PS-201R | TGAGACCTAGACTTTCCCCAGTACTT |
| d6-Des(Otfebit) | D6DES-706R | CCATATCGTGCCTCACTTTTTG |
| d6Elo(Pp_GA) | D6Elo-345R | CCACAAGGAATATCTCCAGGTGAT |
| d6Elo(Tp_GA) | D6Elo-330R | TGGATCGTTCACGTTGAAGTG |
| d5DES(Tc_GA) | D5DES-695R | AAAGCAACGAGTGGCAAGGT |
| d5DES(Tc_GA)3' | D5DES-1200R | AGAGAGCCTCAACTCTTGGAGAGA |
| o3DES(Pi_GA2) | o3DES-652R | TCTTAAGTCCCAACTGGAGAGACA |
| o3DES(PIR_GA) | o3DESPIR-262R | AAACCAAGGAGCGTCAAGTCTAGA |
| d5Elo(Ot_GA3) | MA55 | CGTGTACCACCACGCTTTGT |
| d4DES(TC_GA) | D4DES-Tc-988R | AACACGGTCAAAGCCTTCATAATC |
| d4Des(Eg_GA) | D4DES-Eg-R | ACTTTTCACCACCGACGAAGTT |

TABLE PCR3-continued

| Reverse primers used for qPCR | | |
|---|---|---|
| Target of Interest | Reverse Primer Name | Reverse Primer Oligo |
| d4Des(PI_GA2) | D4DES-PI-817R | CCTCCCACCTCCAAGCAA |
| GPI | Exp 3-128R | CTTGCATGATGATCAGGAAAGC |

Example 4

According to the procedures in example 3 mRNA concentrations in seed were determined for each event at various times after flowering. Tables QPCR1 and QPCR2 describe the amounts of mRNA coding for Delta-5 elongase and Delta-5 desaturase genes, respectively. Missing values indicated that no measurements were taken at the respective day for the plants of the respective event. The mRNA concentrations are given in arbitrary units; within each table QPCR1 and QPCR2 the values are thus commensurate; absolute values cannot be compared within tables but comparisons can be validly made for tendencies and trends.

Table QPCR1 shows that expression of the only Delta-5 elongase gene of the events LBFGKN and LBFLFK continued even after 30 days after flowering, whereas expression of the Delta-5 elongase gene of the events LANPMZ and LAODDN was severely reduced or only marginally detectable after 30 days of flowering. Table QPCR2 shows that for all events clearly detectable Delta-5 desaturase mRNA could be detected at all assay dates.

TABLE QPCR1

| Total Delta-5 elongase (d5Elo(Ot_GA3)) mRNA quantity, assay-specific units | | | | |
|---|---|---|---|---|
| Days after | event | | | |
| flowering | LANPMZ | LAODDN | LBFGKN | LBFLFK |
| 14 | 13.3 | 14.5 | 11.0 | 20.7 |
| 17 | | 55.7 | 10.1 | 6.0 |
| 18 | 15.7 | | | |
| 21 | 38.8 | 66.8 | 29.4 | 55.5 |
| 24 | | 53.6 | 9.5 | 40.1 |
| 25 | 19.7 | | | |
| 28 | 15.7 | 26.6 | 10.0 | 45.1 |
| 31 | | 10.6 | 13.4 | 23.6 |
| 32 | 0.9 | | | |
| 35 | 0.9 | 0.8 | 10.5 | 17.9 |
| 38 | | 9.0 | 10.2 | 13.3 |
| 39 | 0.5 | | | |
| 42 | 1.3 | 1.7 | 19.1 | |
| 45 | | 0.9 | 10.4 | 30.8 |
| 46 | 1.5 | | | 35.7 |

TABLE QPCR2

| Total Delta-5 desaturase mRNA quantity, assay-specific units | | | | |
|---|---|---|---|---|
| Days after | Event | | | |
| flowering | LANPMZ | LAODDN | LBFGKN | LBFLFK |
| 14 | 55.0 | 72.7 | 80.9 | 124.4 |
| 17 | | 168.0 | 98.1 | 45.0 |
| 18 | 70.5 | | | |
| 21 | 199.2 | 364.7 | 302.5 | 292.6 |
| 24 | | 308.6 | 453.4 | 722.4 |
| 25 | 388.1 | | | |
| 28 | 615.8 | 864.2 | 440.8 | 1767.1 |
| 31 | | 2072.5 | 763.8 | 1076.8 |
| 32 | 996.8 | | | |
| 35 | 452.9 | | 578.6 | 558.3 |
| 38 | | 2987.3 | 391.5 | 302.6 |
| 39 | 369.1 | | | |
| 42 | 497.4 | 914.4 | 602.8 | |
| 45 | | 679.0 | 472.5 | 762.9 |
| 46 | 385.7 | | | 1396.4 |

Example 5: Lipids Composition Data

The composition of seed lipids of the events was analysed as described above in example 2. As can be seen in Table FA1, the content of ARA in total extracted seed lipids of events LANPMZ and LAODDN did not significantly decrease over time, whereas the content of ARA ARA in total extracted seed lipids of events LBFGKN and LBFLFK decreases by 0.53% and 0.72%, respectively. Table FA2 shows that EPA content continued to increase in total extracted seed lipids for all events; Table FA3 shows that also DHA content increased in total extracted seed lipids for all events.

Table FA4 summarizes the seed lipids compositions in the last extracts obtained for each event. The table shows that only for events LBFGKN and LBFLFK a difference in EPA and ARA content of more than 5% could be achieved and a difference in (EPA+DHA) and ARA content of more than 7% could be achieved.

TABLE FA1

| ARA content of seed lipids | | | | |
|---|---|---|---|---|
| Days after | event | | | |
| flowering | LANPMZ | LAODDN | LBFGKN | LBFLFK |
| 14 | 0.1 | 0.1 | 0.2 | 0.2 |
| 17 | | 0.3 | 0.3 | 0.6 |
| 18 | 0.9 | | | |
| 21 | 2.0 | 0.9 | 1.2 | 1.9 |
| 24 | | 1.2 | 1.8 | 2.5 |
| 25 | 2.8 | | | |
| 28 | 3.1 | 1.5 | 2.6 | 3.0 |
| 31 | | 1.5 | 3.0 | 3.3 |
| 32 | 3.3 | | | |
| 35 | 3.6 | 1.48 | 2.8 | 3.1 |
| 38 | | 1.4 | 2.6 | 2.8 |
| 39 | 3.6 | | | |

TABLE FA1-continued

ARA content of seed lipids

| Days after flowering | event | | | |
|---|---|---|---|---|
| | LANPMZ | LAODDN | LBFGKN | LBFLFK |
| 42 | 3.6 | 1.4 | 2.6 | |
| 45 | | 1.3 | 2.5 | 2.6 |
| 46 | 3.6 | | | 2.5 |

TABLE FA2

EPA contents of seed lipids

| Days after flowering | event | | | |
|---|---|---|---|---|
| | LANPMZ | LAODDN | LBFGKN | LBFLFK |
| 14 | 0.1 | 0.2 | 0.1 | 0.0 |
| 17 | | 0.4 | 0.4 | 1.0 |
| 18 | 0.7 | | | |
| 21 | 1.7 | 1.6 | 2.0 | 3.3 |
| 24 | | 2.4 | 3.2 | 4.8 |
| 25 | 3.2 | | | |
| 28 | 3.9 | 3.2 | 4.7 | 6.2 |
| 31 | | 4.0 | 6.1 | 7.5 |
| 32 | 4.7 | | | |
| 35 | 5.2 | 4.53 | 6.7 | 7.8 |
| 38 | | 4.6 | 6.8 | 8.1 |
| 39 | 5.3 | | | |
| 42 | 5.5 | 4.9 | 7.3 | |
| 45 | | 4.5 | 7.6 | 8.3 |
| 46 | 5.6 | | | 8.6 |

TABLE FA3

DHA seeds lipid content

| Days after flowering | event | | | |
|---|---|---|---|---|
| | LANPMZ | LAODDN | LBFGKN | LBFLFK |
| 14 | 0.0 | 0.0 | 0.0 | 0.0 |
| 17 | | 0.0 | 0.1 | 0.2 |
| 18 | 0.1 | | | |
| 21 | 0.3 | 0.2 | 0.4 | 0.4 |
| 24 | | 0.3 | 0.5 | 0.6 |
| 25 | 0.5 | | | |
| 28 | 0.7 | 0.5 | 0.8 | 0.8 |
| 31 | | 0.7 | 1.1 | 1.0 |
| 32 | 0.9 | | | |
| 35 | 1.1 | 0.87 | 1.4 | 1.1 |
| 38 | | 1.0 | 1.4 | 1.2 |
| 39 | 1.2 | | | |
| 42 | 1.3 | 1.0 | 1.6 | |
| 45 | | 0.9 | 1.7 | 1.3 |
| 46 | 1.3 | | | 1.4 |

TABLE FA4 composition of last lipids extract obtained for each event

| Content of: | Event | | | |
|---|---|---|---|---|
| | LANPMZ | LAODDN | LFGKN | LBLFK |
| EPA | 5.55 | 4.54 | 7.64 | 8.57 |
| DHA | 3 | 2.46 | 2.39 | 3.61 |
| ARA | 3.59 | 1.26 | 2.47 | 2.54 |
| EPA − ARA | 1.96 | 3.28 | 5.17 | 6.03 |
| (EPA + DHA) − ARA | 4.96 | 5.74 | 7.56 | 9.64 |

The invention claimed is:

1. Brassica napus plant or part thereof, comprising seeds that comprise lipids including eicosapentaenoic acid (EPA) and docosahexaenoic acid (DHA) and optionally arachidonic acid (ARA), wherein
   a) the content of EPA is at least 5% higher than of ARA, and/or
   b) the sum of contents of EPA+DHA is at least 7% higher than ARA and/or
   c) the content of ARA is less than 4% and the content of EPA is more than 7% and the content of DHA is more than 2%, and
   wherein the Brassica napus plant or part thereof comprises a Delta-5 elongase gene under the control of a FAE promoter.

2. Method of altering plant seed lipids composition, comprising the step of growing a Brassica napus plant according to claim 1 to produce seeds that comprise lipids including eicosapentaenoic acid (EPA) and docosahexaenoic acid (DHA) and arachidonic acid (ARA), wherein the step of growing and lipids production is continued until the content of ARA in the lipids of the seeds has decreased.

3. Method of producing a Brassica napus plant seed lipid composition, comprising the steps of
   a) growing Brassica napus plants according to claim 1,
   b) harvesting the plants or a part thereof when the lipids content of ARA in the lipids of the seeds has decreased.

4. Method according to claim 2, wherein ARA in the lipids of the seeds decreases by at least 0.5 wt.-%.

5. The Brassica napus plant or part thereof of claim 1, wherein the content of EPA is at least 5% higher than of ARA in the lipids of the seeds.

6. The Brassica napus plant or part thereof of claim 1, wherein the sum of contents of EPA+DHA is at least 7% higher than ARA in the lipids of the seeds.

7. The Brassica napus plant or part thereof of claim 1, wherein the content of ARA in the lipids of the seeds is less than 4% and the content of EPA in the lipids of the seeds is more than 7% and the content of DHA in the lipids of the seeds is more than 2%.

8. The Brassica napus plant or part thereof of claim 1, wherein expression of the Delta-5 elongase gene is maintained or increased in late stage seed development.

9. Brassica napus plant comprising seeds that comprise lipids including eicosapentaenoic acid (EPA) and docosahexaenoic acid (DHA) and arachidonic acid (ARA), wherein, when the Brassica napus plant or part thereof is grown, the content of ARA in the lipids of the seeds decreases at least 0.5% by weight of total lipids and the content of EPA and/or DHA in the lipids of the seeds increases, wherein the seeds comprise a Delta-5 elongase gene under the control of a FAE promoter.

10. Brassica napus plant according to claim 9, wherein the content of EPA in the lipids of the seeds increases at least 1.0% by weight of total lipids during late stage seed development.

11. The Brassica napus plant of claim 9, wherein, when the Brassica napus plant or part thereof is grown, the content of ARA in the lipids of the seeds decreases at least 0.5% by weight of total lipids and the content of EPA and/or DHA in the lipids of the seeds increases during late stage seed development.

* * * * *